US009655513B2

(12) United States Patent
Fabrikant et al.

(10) Patent No.: US 9,655,513 B2
(45) Date of Patent: May 23, 2017

(54) WAVEFRONT MEASUREMENT PRE-SMOOTHING SYSTEMS AND METHODS

(71) Applicant: AMO Development, LLC, Santa Ana, CA (US)

(72) Inventors: Anatoly Fabrikant, Fremont, CA (US); Dimitri Chernyak, Sunnyvale, CA (US); Guang-ming Dai, Fremont, CA (US); Jayesh Shah, Sunnyvale, CA (US)

(73) Assignee: AMO Development, LLC, Santa Ana, CA (US)

( * ) Notice: Subject to any disclaimer, the term of this patent is extended or adjusted under 35 U.S.C. 154(b) by 213 days.

(21) Appl. No.: 14/579,782

(22) Filed: Dec. 22, 2014

(65) Prior Publication Data

US 2015/0182112 A1 Jul. 2, 2015

Related U.S. Application Data

(60) Provisional application No. 61/922,605, filed on Dec. 31, 2013, provisional application No. 61/935,247, filed on Feb. 3, 2014.

(51) Int. Cl.
*A61B 3/10* (2006.01)
*A61F 9/008* (2006.01)

(52) U.S. Cl.
CPC ........ *A61B 3/1015* (2013.01); *A61F 9/00804* (2013.01); *A61F 9/00827* (2013.01);
(Continued)

(58) Field of Classification Search
CPC .................................................. A61B 3/1015
(Continued)

(56) References Cited

U.S. PATENT DOCUMENTS

2005/0107775 A1* 5/2005 Huang .................... A61F 9/008
606/5
2008/0140329 A1 6/2008 Dai
(Continued)

OTHER PUBLICATIONS

Dai, G-M. "Comparison of Wavefront Reconstructions With Zernike Polynomials and Fourier Transforms." *Journal of Refractive Surgery* vol. 22 (2006): pp. 943-948.
(Continued)

*Primary Examiner* — Huy K Mai
(74) *Attorney, Agent, or Firm* — Abbott Medical Optics Inc.

(57) ABSTRACT

Embodiments of the present invention encompass systems and methods for generating a vision treatment target for an eye of a patient. Exemplary techniques can involve obtaining a wavefront measurement for the eye of the patient, processing the wavefront measurement, using a low pass filter, to obtain an ocular wavefront, and generating the vision treatment target based on the ocular wavefront. In some cases, the wavefront is processed by applying a Fourier transform to the wavefront measurement to obtain a Fourier spectrum of the wavefront, convolving, in the Fourier domain, the Fourier spectrum of the wavefront and the low pass filter to obtain a Fourier spectrum convolution result, and applying an inverse transform to the convolution result to obtain the ocular wavefront. The ocular wavefront can represent a low pass filtered version of the wavefront measurement, such that high spatial frequency features present in the wavefront measurement are not present in the ocular wavefront.

18 Claims, 9 Drawing Sheets

(52) U.S. Cl.
CPC ............... *A61F 2009/0087* (2013.01); *A61F 2009/0088* (2013.01); *A61F 2009/00872* (2013.01)

(58) Field of Classification Search
USPC .......................... 351/205, 246, 212; 606/4, 5
See application file for complete search history.

(56) References Cited

U.S. PATENT DOCUMENTS

| | | | |
|---|---|---|---|
| 2009/0219485 A1* | 9/2009 | Sarver ................. | A61B 3/1015 351/221 |
| 2013/0190736 A1 | 7/2013 | Fabrikant et al. | |
| 2014/0095137 A1 | 4/2014 | Dai et al. | |

OTHER PUBLICATIONS

Huang, D., et al. "Mathematical Model of Corneal Surface Smoothing After Laser Refractive Surgery." *American Journal of Ophthalmology* vol. 135, No. 3 (2003): pp. 267-278.

Reinstein, D.Z., et al. "Epithelial Thickness Profile Changes Induced by Myopic LASIK as Measured by Artemis Very High-frequency Digital Ultrasound." *Journal of Refractive Surgery* vol. 25, Issue 5 (2009): pp. 444-450.

International Search Report and Written Opinion for Application No. PCT/US2014/072769, mailed on Mar. 27, 2015, 12 pages.

* cited by examiner

WAVEFRONT MEASUREMENT PRE-SMOOTHING SYSTEMS AND METHODS

CROSS-REFERENCE TO RELATED APPLICATIONS

This application is a non-provisional of and claims the benefit of priority to U.S. Provisional Patent Application No. 61/922,605 filed Dec. 31, 2013 and U.S. Provisional Patent Application No. 61/935,247 filed Feb. 3, 2014, the content of each of which is incorporated herein by reference.

BACKGROUND OF THE INVENTION

Embodiments of the present invention relate to systems and methods for treating vision conditions in a patient, and in particular to techniques for developing targets for use in such treatments.

Current treatment planning procedures often involve taking several wavefront measurements, and using a measurement selection algorithm to select a single one of the wavefront measurements for generating the treatment target. The other non-selected wavefront measurements are not used for treatment planning purposes. Often, the single wavefront measurement which is selected for the treatment plan can include transient small-scale spatial variations.

Although vision treatment techniques that are based on wavefront measurements provide real benefits to patients in need thereof, still further improvements are desirable. Embodiments of the present invention provide solutions for at least some of these outstanding needs.

BRIEF SUMMARY OF THE INVENTION

Wavefront based laser vision correction procedures typically include a diagnostic measurement which evaluates certain aspects of the patient eye. For example, a wavefront measurement may capture details of the eye at a given instance in time. Often, such measurements contain certain high spatial frequency features. In some cases, these features are transient (e.g. tear film) and vary from measurement to measurement. In some cases, these features can be permanent (e.g. corneal scar) such that the high frequency spatial structure is consistent across multiple measurements. Embodiments of the present invention encompass systems and methods for pre-smoothing a wavefront measurement by dampening or eliminating such high frequency features (e.g. 0.3 mm and smaller), for example by using a low pass filter. Embodiments also encompass systems and methods for averaging multiple measurements, which provides an alternative approach to smoothing, by blurring out high frequency features, and in particular transient high frequency features. The modified or ocular wavefront can then be used to develop a treatment target which is applied to the eye. Accordingly, the target shape that is administered to the patient may not identically correspond to any given wavefront measurement.

Often, the pre-smoothing techniques include a convolution protocol that is implemented in the Fourier domain. It is possible to achieve a very high resolution using a Fourier decomposition of the wavefront measurement. Relatedly, the high resolution allows for improved accuracy for both small and large features of the wavefront. In some instances, high resolution Fourier techniques can be used initially in obtaining and processing the wavefront data (e.g. to obtain a Fourier spectrum of the wavefront), and then high frequency information can be dampened or discarded by a pre-smoothing process.

In one aspect, embodiments of the present invention encompass systems and methods for generating a vision treatment target for an eye of a patient. Exemplary methods include obtaining a wavefront measurement for the eye of the patient, processing the wavefront measurement, using a low pass filter, to obtain an ocular wavefront, and generating the vision treatment target based on the ocular wavefront. In some cases, the processing step can include applying a Fourier transform to the wavefront measurement to obtain a Fourier spectrum of the wavefront, convolving, in the Fourier domain, the Fourier spectrum of the wavefront and a low pass filter to obtain a Fourier spectrum convolution result, and applying an inverse transform to the convolution result to obtain the ocular wavefront. The ocular wavefront can represent a low pass filtered version of the wavefront measurement, such that high spatial frequency features present in the wavefront measurement are not present in the ocular wavefront. In some cases, the low pass filter is a Gaussian low-pass filter having a kernel size of 0.3 mm. In some cases, methods may include administering the vision treatment target to the eye of the patient. In some cases, methods may include processing the treatment target with a deconvolution protocol to obtain a deconvolved treatment target. In some cases, methods may include administering the deconvolved treatment target to the eye of the patient.

In another aspect, embodiments of the present invention encompass systems and methods for generating a vision treatment target for an eye of a patient. Exemplary systems include a processor, a first module, an second module, and a third module. The first module can include a tangible medium embodying machine-readable code executed on the processor to obtain a wavefront measurement for the eye of the patient. The second module can include a tangible medium embodying machine-readable code executed on the processor to process the wavefront measurement with a low pass filter to obtain an ocular wavefront. The third module can include a tangible medium embodying machine-readable code executed on the processor to generate the vision treatment target based on the ocular wavefront. In some cases, the tangible medium embodying machine-readable code of the second module, when executed on the processor, applies a Fourier transform to the wavefront measurement to obtain a Fourier spectrum of the wavefront, convolves, in the Fourier domain, the Fourier spectrum of the wavefront and a low pass filter to obtain a Fourier spectrum convolution result, and applies an inverse transform to the convolution result to obtain the ocular wavefront. In some cases, the ocular wavefront represents a low pass filtered version of the wavefront measurement, such that high spatial frequency features present in the wavefront measurement are not present in the ocular wavefront. According to some embodiments, the low pass filter is a Gaussian low-pass filter having a kernel size of 0.3 mm. In some embodiments, systems may also include a fourth module having a tangible medium embodying machine-readable code executed on the processor to administer the vision treatment target to the eye of the patient. In some embodiments, systems may also include a fourth module having a tangible medium embodying machine-readable code executed on the processor to process the treatment target with a deconvolution protocol to obtain a deconvolved treatment target. In some embodiments, systems may also include a fifth module having a tangible medium embodying machine-readable code executed on the processor to administer the deconvolved treatment target to the eye of the patient.

In yet another aspect, embodiments of the present invention encompass computer products embodied on tangible computer readable storage media. An exemplary computer product embodied on tangible computer readable storage medium may include code for obtaining a wavefront measurement for the eye of the patient, code for processing the wavefront measurement, using a low pass filter, to obtain an ocular wavefront, and code for generating the vision treatment target based on the ocular wavefront. In some cases, the code for processing the wavefront measurement includes code for applying a Fourier transform to the wavefront measurement to obtain a Fourier spectrum of the wavefront, code for convolving, in the Fourier domain, the Fourier spectrum of the wavefront and a low pass filter to obtain a Fourier spectrum convolution result, and code for applying an inverse transform to the convolution result to obtain the ocular wavefront. The ocular wavefront represents a low pass filtered version of the wavefront measurement, such that high spatial frequency features present in the wavefront measurement are not present in the ocular wavefront. In some cases, the low pass filter is a Gaussian low-pass filter having a kernel size of 0.3 mm. In some cases, computer products may also include code for administering the vision treatment target to the eye of the patient. In some cases, computer products may also include code for processing the treatment target with a deconvolution protocol to obtain a deconvolved treatment target. In some cases, computer products may also include code for administering the deconvolved treatment target to the eye of the patient.

DETAILED DESCRIPTION OF THE INVENTION

Figure 1:
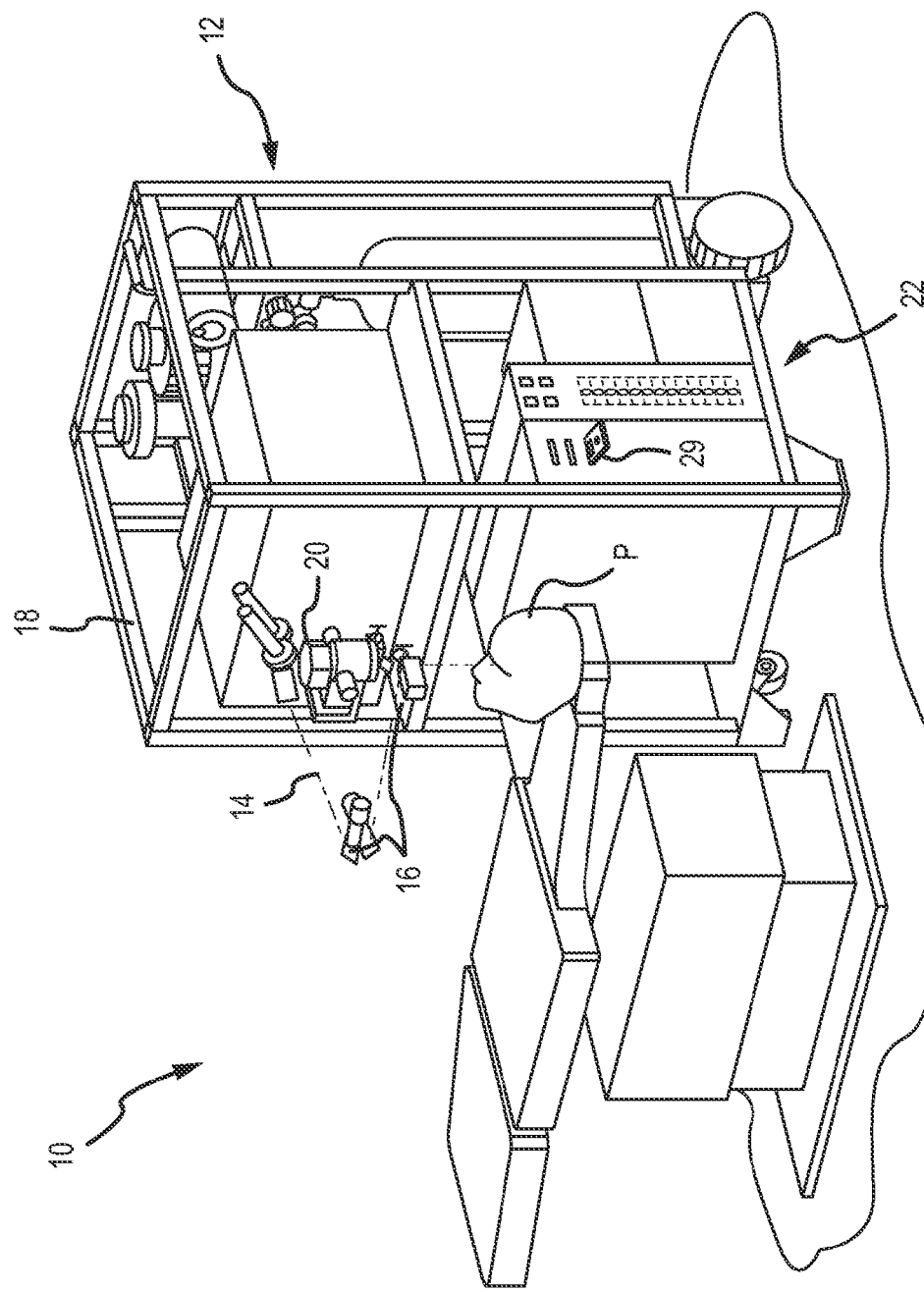
FIG. 1 illustrates a laser ablation system according to an embodiment of the present invention.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like. In some cases, embodiments provide techniques for using laser basis data during refractive surgery treatment procedures which can be implemented in such laser devices.

Exemplary systems and methods disclosed herein can be implemented via a variety of ophthalmic devices or solutions. For example, treatment techniques may be used for any of a variety of surgery modalities, including excimer laser surgery, femtosecond surgery, and the like. A variety of forms of lasers and laser energy can be used to effect a correction or treatment, including infrared lasers, ultraviolet lasers, femtosecond lasers, wavelength multiplied solid-state lasers, and the like. By way of non-limiting example, ophthalmic corrections can involve a cornea or lens reshaping procedure, such as, for example using a picosecond or femtosecond laser. Laser ablation procedures can remove a targeted amount stroma of a cornea to change a cornea's contour and adjust for aberrations. In some cases, a treatment protocol can involve the delivery of a series of discrete pulses of laser light energy, with a total shape and amount of tissue removed being determined by a shape, size, location, and/or number of laser energy pulses impinging on or focused within a cornea. In some cases, a surgical laser, such as a non-ultraviolet, ultra-short pulsed laser that emits radiation with pulse durations as short as nanoseconds and femtoseconds (e.g., a femtosecond laser, or a picosecond laser) can be used to treat the eye of a patient. Other pulse widths may be suitable as well. The laser systems can be configured to deliver near infrared light. Other wavelengths may be used as well. The laser systems can be configured to deliver laser light focused at a focus depth (e.g. within corneal or other ophthalmologic tissue) which may be controlled by the system. Laser surgery with ultra-short pulse lasers such as femtosecond lasers can be used to treat the eye. These pulsed lasers can make very accurate incisions of the eye and can be used in many ways to treat the eye. Additional types of incisions that can be performed with the short pulse lasers include incisions for paracentesis, limbal relaxing incisions, and refractive incisions to shape the cornea, for example.

In some cases, vision treatments can include focusing femtosecond laser energy within the stroma so as to ablate a volume of intrastromal tissue. By scanning the focal spot within an appropriate volume of the stromal tissue, it is possible to vaporize the volume so as to achieve a desired refractive alteration. Hence, embodiments of the present invention encompass laser surgical techniques that involve femtosecond laser photodisruption or photoalteration treatments. In some cases, a femtosecond laser can be used to perform the photodisruption, thus providing an easy, precise, and effective approach to refractive surgery.

According to some embodiments, a femtosecond laser (or other laser) of the optical system can be used to incise the cornea or to cut a flap. A femtosecond laser may be used to make arcuate or other incisions in the cornea, which incisions may be customized, intrastromal, stable, predictable, and the like. Likewise, corneal entry incisions may be made, which are custom, multi-plane, and self-sealing.

Pulsed laser beams include bursts or pulses of light. Pulsed lasers, such as non-ultraviolet, ultra-short pulsed lasers with pulse durations measured in the nanoseconds to femtoseconds range, can be used in ophthalmic surgical procedures as disclosed herein. For example, a pulsed laser beam can be focused onto a desired area of ophthalmologic material or tissue, such as the cornea, the capsular bag, or the lens of the eye, to photoalter the material in this area and, in some instances, the associated peripheral area. Examples of photoalteration of the material include, but are not necessarily limited to, chemical and physical alterations, chemical and physical breakdown, disintegration, ablation, photodisruption, vaporization, a the like. Exemplary treatment systems can include a focusing mechanism (e.g. lens) and/or a scanning mechanism so as to guide or direct a focus of femtosecond energy along a path within the patient's eye (e.g. at one or more corneal subsurface locations).

According to some embodiments, the vergence weighting systems and methods disclosed herein can be implemented in connection with software, hardware, or a combination of software and hardware residing in a diagnostic device such as WaveScan® and iDesign™ devices.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
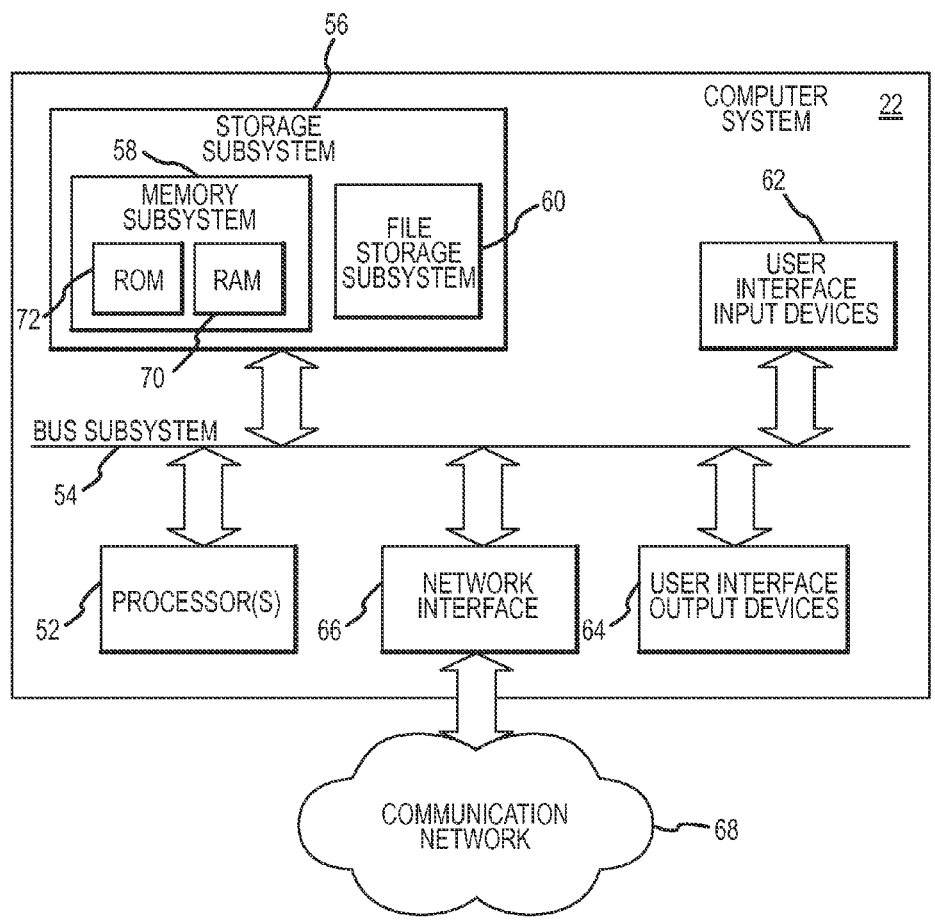
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
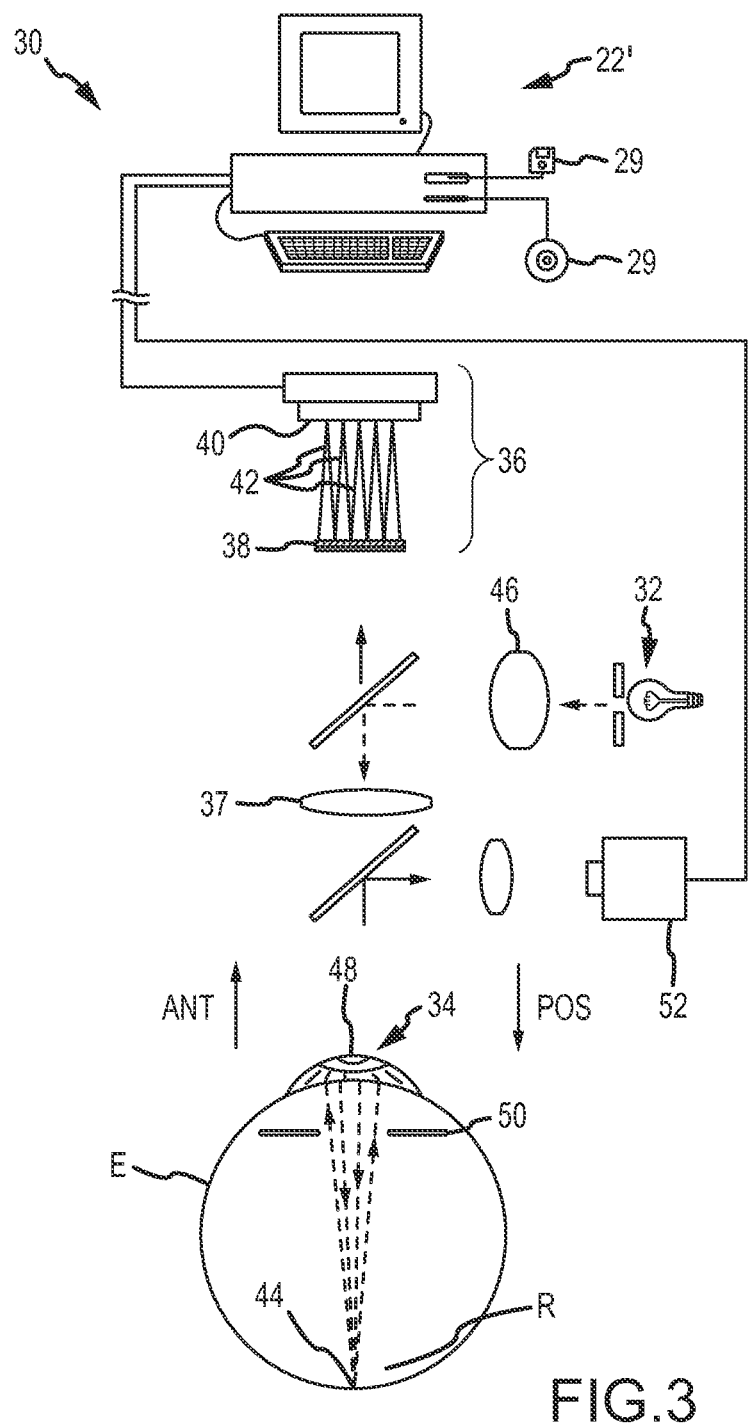
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program.

Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
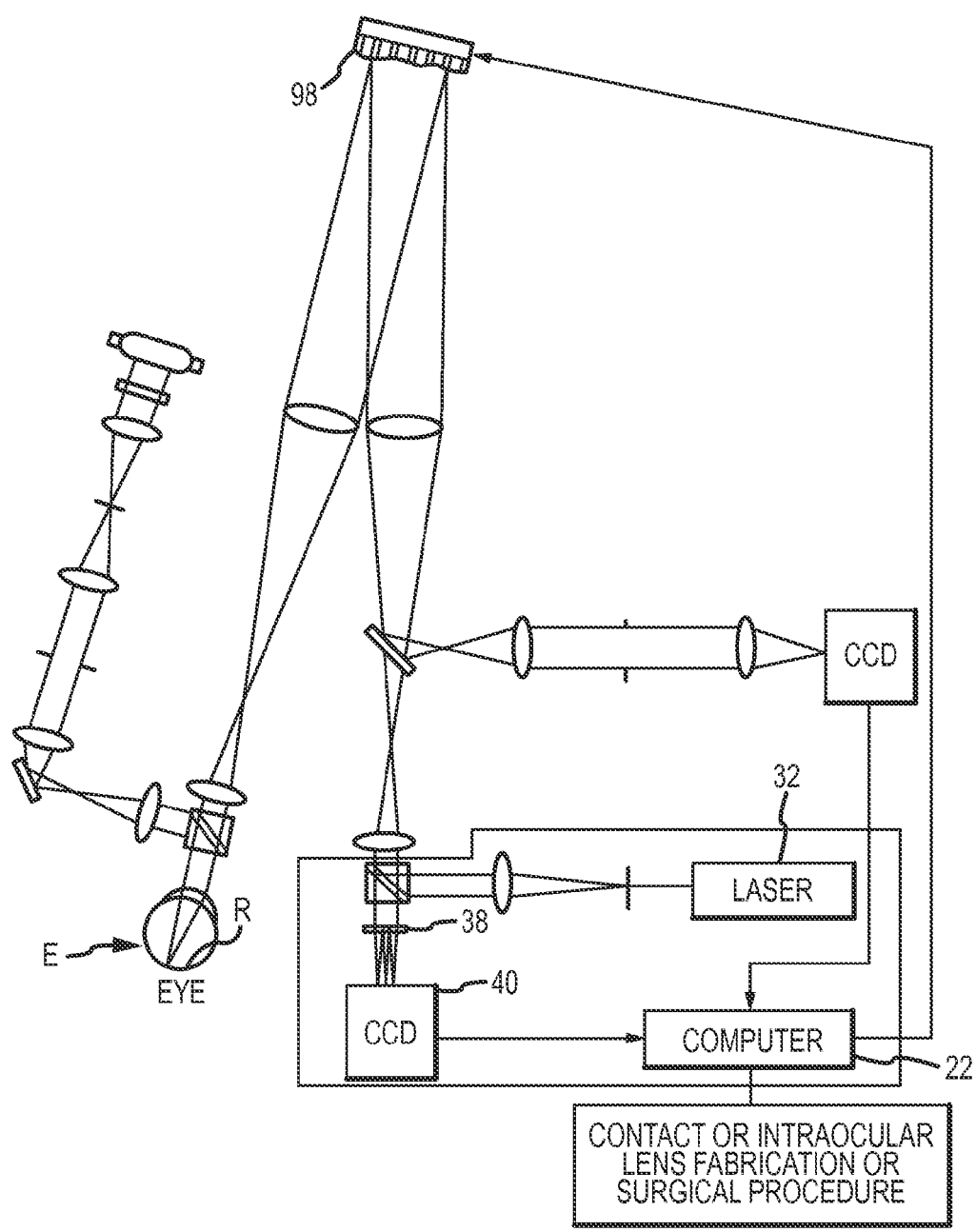
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO MANUFACTURING USA, LLC, MILPITAS, California. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Wavefront Pre-Processing

Figure 4:
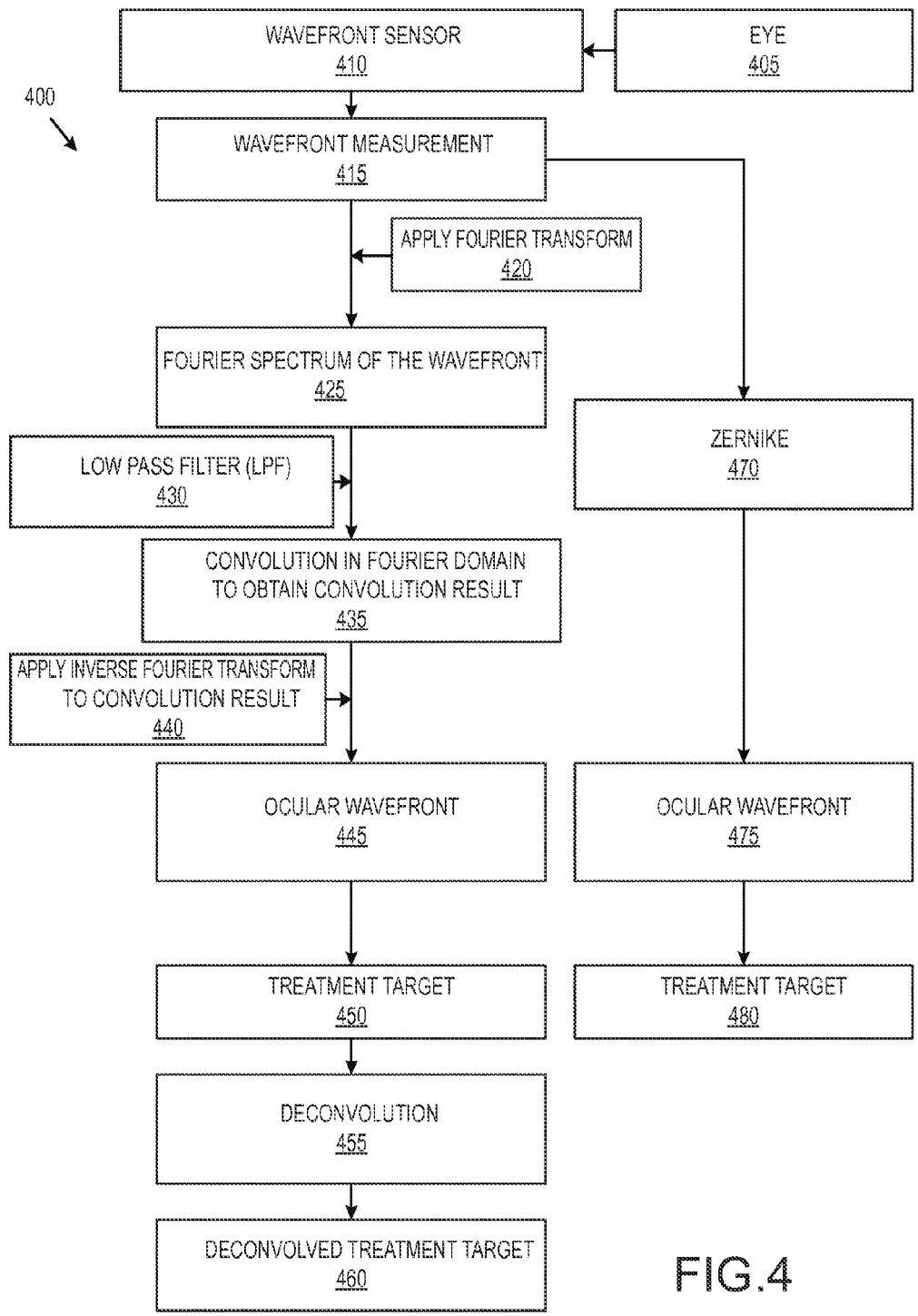
FIG. 4 shows aspects of a method for generating at treatment target or plan according to embodiments of the present invention.

Embodiments of the present invention encompass systems and methods for adjusting or generating wavefront-based refractive treatment plans which involve the pre-processing of wavefront information or measurements. As depicted in FIG. 4, an exemplary method 400 of generating at treatment target or plan can include obtaining a wavefront measurement 415 for an eye 405 of a patient. Often, the eye may present high spatial frequency features, including transient features such as tear film, as well as permanent features such as corneal scars. As discussed elsewhere herein, it is possible to ignore or filter out certain small-scale spatial variations. The wavefront measurement 415 may be obtained, for example, by evaluating the eye 405 with a wavefront sensor device 410. A wavefront sensor 410 may include an array of lenslets, and the configuration of the lenslet array can determine the resolution of the sensor. For example, a lower density resolution sensor may have a lenslet array with wider spacing, and a higher density resolution sensor may have a lenslet array with narrower spacing. The wavefront sensor 410 can be configured to detect high spatial frequency features, including rapid curvature changes and the like. As discussed elsewhere herein, embodiments of the present invention can operate to ignore or suppress certain high spatial frequency information obtained by the wavefront device. In some instances, a filter can be used to suppress this information, in a way that is consistent for all measurements (e.g. independent of the resolution of the sensor, and independent of the wavefront diameter). Hence, a wavefront measurement having a very high resolution can be processed with a Fourier transform (or some other zonal reconstruction methods), and an LPF filter can be applied according to a defined spatial scale for smoothing. According to some embodiments, the wavefront measurement can include gradient information. For example, slope sensors of the wavefront sensor 410 can operate to generate local gradient measurements. Relatedly, the wavefront measurement can include a wavefront gradient field based on the local gradients.

As depicted as step 420, methods may include applying a Fourier transform to the wavefront measurement 415, so as to obtain a Fourier transform 425 of the wavefront. For example, by applying the Fourier transform of step 420, it is possible to obtain a Fourier transform of the local wavefront gradient measurements. A Fourier transform can be used to reconstruct wavefront data by decomposing the image into spatial frequency components. As noted elsewhere herein, the Fourier spectrum of the wavefront 425 can provide a high resolution representation of the wavefront.

By using the Fourier approach, it is possible to ensure that the shape being measured by the aberrometer is an accurate representation of the optics of the eye. The Fourier transform technique provides an alternative to Zernike polynomials, and can be used to precisely reconstructed the wavefront. Using the Fourier method, it is possible to sample the wavefront over fixed intervals of space that correspond to the equal spacing of the lenslets in the sensor's lenslet array. Hence, the Fourier technique is well suited for use with an evenly spaced grid such as the Hartmann-Shack sensor. Further, Fourier transform techniques are not limited to a circular reconstruction, and hence can accommodate elliptical pupil apertures. What is more, surgeons or operators are not required to specify the order of the reconstruction, as typically is the case with Zernike reconstruction. As discussed elsewhere herein, the Fourier reconstruction can use all the data present in the reconstruction, thus providing a high resolution representation. Relatedly, the Fourier technique is capable of accurately characterizing a broad range of optical aberrations.

According to some embodiments, a Fourier series can be used as a set of basis functions for the ocular wavefront reconstruction. Exemplary methods can include obtaining the wavefront slopes in x- and y-directions, and taking the Fourier transform of these wavefront slopes. Once the Fourier transform, or the Fourier spectrum of the wavefront, is obtained, it is then possible to obtain the ocular wavefront by an inverse Fourier transform of the Fourier transform of the wavefront.

According to step 430, methods may also include provising a low pass filter (LPF), which can operate to remove high spatial frequency data or variations of the wavefront. In some cases, a Gaussian kernel may be used. In some cases, a single parameter Butterworth kernel may be used. In some cases, a dual parameter or multiple parameter kernel may be used. Exemplary filter, kernels, and related techniques are discussed in U.S. Patent Application No. 61/708,815 filed Oct. 2, 2012, U.S. Patent Application No. 61/871,120 filed Aug. 28, 2013, U.S. patent application Ser. No. 14/044,650 filed Oct. 2, 2013, and U.S. Patent Application No. 61/901,216 filed Nov. 7, 2013, the contents of each of which are incorporated herein by reference.

The low pass filter (LPF) can be used to remove or reduce small-scale spatial variations (e.g. high spatial frequency features) associated with the measured wavefront, for example by processing the measured wavefront information with LPF prior to using the measured wavefront information in the treatment planning protocol. Typically, although the small-scale spatial variations are removed, the low order and high order aberration information is retained. According to some embodiments, a Gaussian low-pass filter having a kernel size of 0.3 mm can be used. Such a filter produced little or no change in the low-order and high-order aberrations, and can smooth out any features smaller than 0.3 mm, thus improving the robustness and efficiency of the generated treatment.

In some cases, the smoothing kernel size may correspond to a spatial frequency cutoff in the frequency domain. For example, with a pupil that is 6 mm in diameter (which is typical), the Airy disk can be about 0.38 arc minutes, which corresponds to about 79 cycles per degree (cutoff frequency) in the frequency domain. If the aberrometer lenslet spacing is 0.175 mm or so, a 0.3 mm in size on the cornea corresponds to about 0.3/0.175, or 1.7 times the lenslet spacing. Therefore, 0.3 mm can correspond to 1.7 times smaller than the cutoff frequency of 79 cpd, which is about 46 cpd. Hence, using a low pass filter kernel size of 0.3 mm for a 6 mm pupil (or measured wavefront diameter) can suppress or remove high spatial frequency structures that are higher than about 46 cpd.

According to some embodiments, this cutoff number can change with different pupil sizes. For example, with a smaller pupil, this 0.3 mm (i.e. kernel size) is a bigger relative portion so it corresponds to a lower frequency number. For example, for a 5 mm pupil, 0.3 mm corresponds to only about 38 cpd. Hence, using a low pass filter kernel size of 0.3 mm for a 5 mm pupil (or measured wavefront diameter) can suppress or remove high spatial frequency structures that are higher than about 38 cpd.

For a very small pupil, say, 2 mm in diameter, 0.3 mm corresponds to 15 cpd, which is not very high spatial frequency. 15 cpd corresponds to about 20/40 in visual acuity. According to some embodiments, for a pupil size of 4 mm or smaller, it may be desirable to use a smoothing kernel size that is different from 0.3 mm, since the smoothing in principle may inhibit the correction better than 30 cpd, or 20/20. Typically, however, patients rarely present with a pupil size (or a measured wavefront diameter) smaller than 4 mm.

Use of a 0.3 mm cutoff scale can be based on physiological parameters. For example, scales of this size or smaller can eventually disappear during after-treatment healing. Hence, it may not be desirable to ablate the cornea with a target that has features smaller than 0.3 mm. In some cases, a low pass filter can be applied to remove high spatial frequency structures within a certain range of sizes or dimensions, between an upper threshold and a lower threshold. For example, it is possible to apply a band-pass filter to limit certain sections of frequencies. In some cases, a lower threshold can have a value that is greater than the 0 frequency. In some cases, a low pass filter can operate to limit a spatial frequency band, for example to dampen artificial noises introduced by a wavefront device.

In some instances, the low pass filter can be based on various factors, including the ability of the laser to ablate, the actual smoothing of the cornea after surgery, tracking and/or registration features of the laser delivery system, and the like. For example, it is possible to define the spatial dimension of the filter in a way that takes into account the cell sizes, the epithelial layer, or other biological parameters.

Embodiments of the present invention encompass systems and methods for implementing the low pass filter in the Fourier domain. For example, when a wavefront is reconstructed from a Fourier spectrum, small-scale spatial features of the measured wavefront can be reduced or removed when the wavefront spectrum is multiplied by the LPF spectrum.

As shown in step 435, methods can include performing a convolution in the Fourier domain (e.g. spectral domain or frequency domain). For example, methods may include multiplying the wavefront spectrum provided in step 425 and the LPF spectrum provided in step 430, so as to obtain a convolution result. According to some embodiments, a corresponding convolution may also be performed in the spatial domain, rather than in the Fourier domain. For example, a convolution operation in the spatial domain can involve a multiplication step. In contrast, a convolution in the Fourier domain can involve a Fourier transform of the objects to be convolved, followed by a multiplication step that involves multiplying the Fourier spectrum components (e.g. convolution kernel or low pass filter multiplied by Fourier transform of wavefront) on a pixel by pixel basis, followed by an inverse Fourier transform step. The inverse Fourier transform can operate to transform the frequency domain function to a spatial domain function. The pre-smoothing technique can operate to attenuate or suppress the high spatial frequency features.

As shown in step 440, methods can further include applying an inverse Fourier transform to the convolution result obtained in step 435. In this way, it is possible to obtain the ocular wavefront 445. Hence, the ocular wavefront can represent a reconstructed gradient field, which is provided by obtaining the inverse Fourier transform of the Fourier transform. According to some embodiments, the Fourier transform can be represented by the convolution result 435. Put another way, by applying the inverse Fourier transform, it is possible to obtain the ocular wavefront 445, which can be considered to be a low pass filtered version (spatial domain) of the wavefront measurement 415 (spatial domain).

Further, methods can include determining a treatment target 450 based on the ocular wavefront, and applying a deconvolution to the treatment target as indicated by step 455, so as to obtain a deconvolved treatment target 460. Exemplary deconvolution techniques are discussed in U.S. Patent Application No. 61/708,815 filed Oct. 2, 2012, U.S. Patent Application No. 61/871,120 filed Aug. 28, 2013, U.S. patent application Ser. No. 14/044,650 filed Oct. 2, 2013, and U.S. Patent Application No. 61/901,216 filed Nov. 7, 2013, the contents of each of which are incorporated herein by reference. In some instances, the deconvolution technique can be selected based on a model of what occurs in the eye following surgery. For example, the deconvolution procedure of step 455 can operate to account for healing and biomechanical changes. In some instances, a deconvolution process 455 can operate to amplify small-scale spatial features. Hence, a pre-smoothing protocol to obtain the ocular wavefront 445 can be helpful to avoid the presence of such small-scale spatial features, which may pertain to transient high spatial frequency information, when performing the deconvolution.

According to some embodiments, a treatment target 450 can be used for laser surgery, without performing the deconvolution process of step 455.

FIG. 4 also depicts an alternative approach for determining a treatment target 450. For example, a Zernike representation for the wavefront measurement 415 can be generated, as indicated by step 470. In some cases, it is possible to represent a wavefront using a number of higher-order Zernike polynomials. Typically, this step involves taking into account the pupil size, and also involves specifying the order of the reconstruction (e.g. $6^{th}$, $8^{th}$, or $10^{th}$), which can suppress high spatial frequency information. For example, Zernikes up to a certain order do not contain high spatial frequency information, and hence Zernike decomposition/reconstruction techniques can operate to reduce high frequency information. For example, in some cases, it may be difficult to represent a wavefront having very steep gradients or very high spatial frequency structure with Zernike polynomials, due to the presence of the of fine spatial definition in the wavefront measurement. Zernike approaches may require implementation using a particular aberrometer, and a particular pupil size, because for individual reconstructions the limit of high spatial frequency information may depend on the specific eye. Accordingly, Zernike techniques may be more difficult to implement from a system point of view, because requirements may vary depending on the number of orders needed for reconstruction, the hardware used (e.g. aberrometer), the pupil size of the eye, and the like. As indicated in step 475, the alternative approach can also include obtaining an ocular wavefront based on the Zernike representation. For example, a reconstructed gradient field can be generated based on a Zernike representation which is expressed in the form of a polynomial function. The alternative approach can also include generating a treatment target 480 based on the ocular wavefront 475. Optionally, the treatment target 480 can be processed with a deconvolution protocol so as to obtain a deconvolved treatment target. In some cases, it is possible to provide an ocular wavefront 445 for generating a treatment target, and an ocular wavefront 475 for diagnostic purposes. That is, the ocular wavefront 475 can be used to generate a map or representation for use in a diagnostic application (e.g. in conjunction with the development of a treatment target 450 for administration to a patient), without generating a treatment target 480 based on the ocular wavefront 475.

Figure 4A:
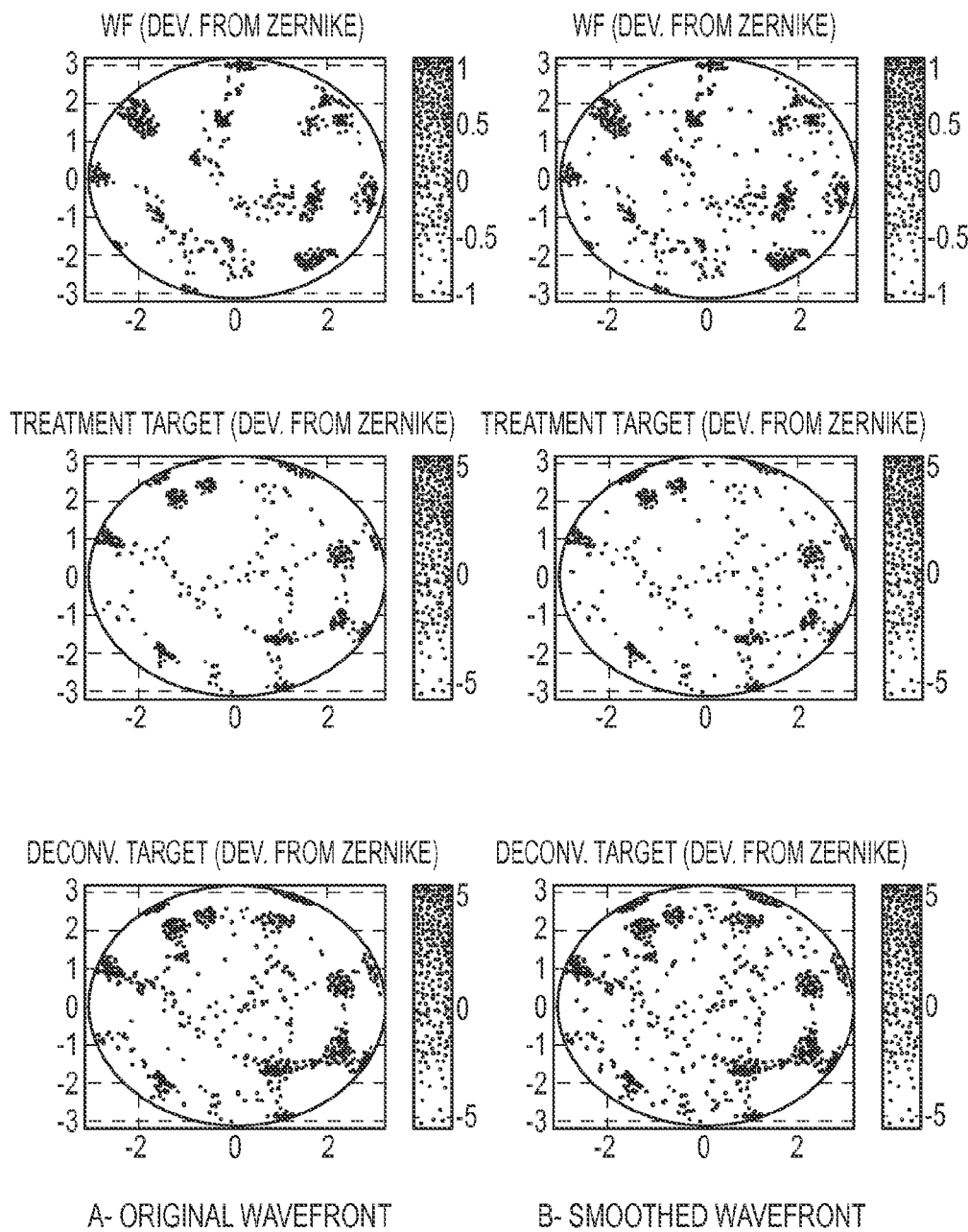
FIG. 4A depicts aspects of wavefront and target representations according to embodiments of the present invention.

FIG. 4A depicts wavefront representations (top panel), ablation treatment target representations (middle panel), and deconvolved target representations (bottom panel), for original wavefronts (left side) and smoothed wavefronts (right side). The wavefront and target representations are depicted in terms of deviations from a $6^{th}$ order Zernike reconstruction technique. As shown here, there is a wavefront smoothing effect on small-scale features in a Fourier wavefront and a corresponding ablation target (WFD=6.4 mm, Sph=−7.25D, Cyl=−1.5D). For example, it can be seen that in the smoothed wavefront representations (right side) there is a lower amount of devisation from the Zernike reconstruction. The sharp boundaries are smoothed, and some small and sharp features are dampened or removed on the right side panels, as compared to the left side panels. Wavefront representations used for treatment planning can be created with Fourier decomposition, which can resolve small-scale features down to 0.14 mm size. Such features can also be reflected in the ablation target as shown in FIG. 4A. Deconvolution techniques (e.g. such as those shown in step 455 of FIG. 4), can amplify such small-scale features, which may lead to increased number of pulses and treatment time or cause other unwanted effects in a treatment plan. Removing such small-scale features from the wavefront measurement can be helpful, because such features can transiently change from one wavefront measurement to another, and corneal smoothing often erases any small-scale features of less than 0.3 mm size after several months. As discussed elsewhere herein, pre-smoothing can be implemented for Fourier reconstruction techniques, and can also be implemented for zonal reconstruction techniques. In such cases, artificial high frequency information that is not ideal may be introduced, and it may be desirable to not amplify that information when developing a treatment target.

After pre-smoothing of the wavefront, the de-convolved target does not reveal sharp small-scale features, which were in the original Fourier wavefront as shown in FIG. 4A. Moreover, such removal of high spatial frequency information from the wavefront measurement can save time and increase the efficiency of a laser treatment, regardless of whether a deconvolution protocol is applied. For example, by reducing or eliminating the presence of such features from the treatment target 450, the laser fitting algorithm does not need to account for these features when implementing the treatment. Hence, the number of smaller pulses and/or the ablation time can be reduced. In this way, the treatment target 450 can be more easily implemented by a laser, without requiring tiny fluctuations (e.g. that are smaller than the width of a laser pulse), such that the laser can more efficiently create the desired surface shape on the eye. Put another way, by providing a treatment target that does not require extremely small laser pulse sizes, it is easier to deliver the pulses in the desired locations accurately, particularly in the context of other system features such as eye tracking and iris registration techniques, as the capability of these system parameters may not match the requirements for the accurate delivery of extremely small pulse sizes at precise locations. According to some embodiments of the present invention, a treatment target 450 or 460 can be developed, where the smallest pulse size is no less than 0.5 mm in diameter.

Figure 4B:
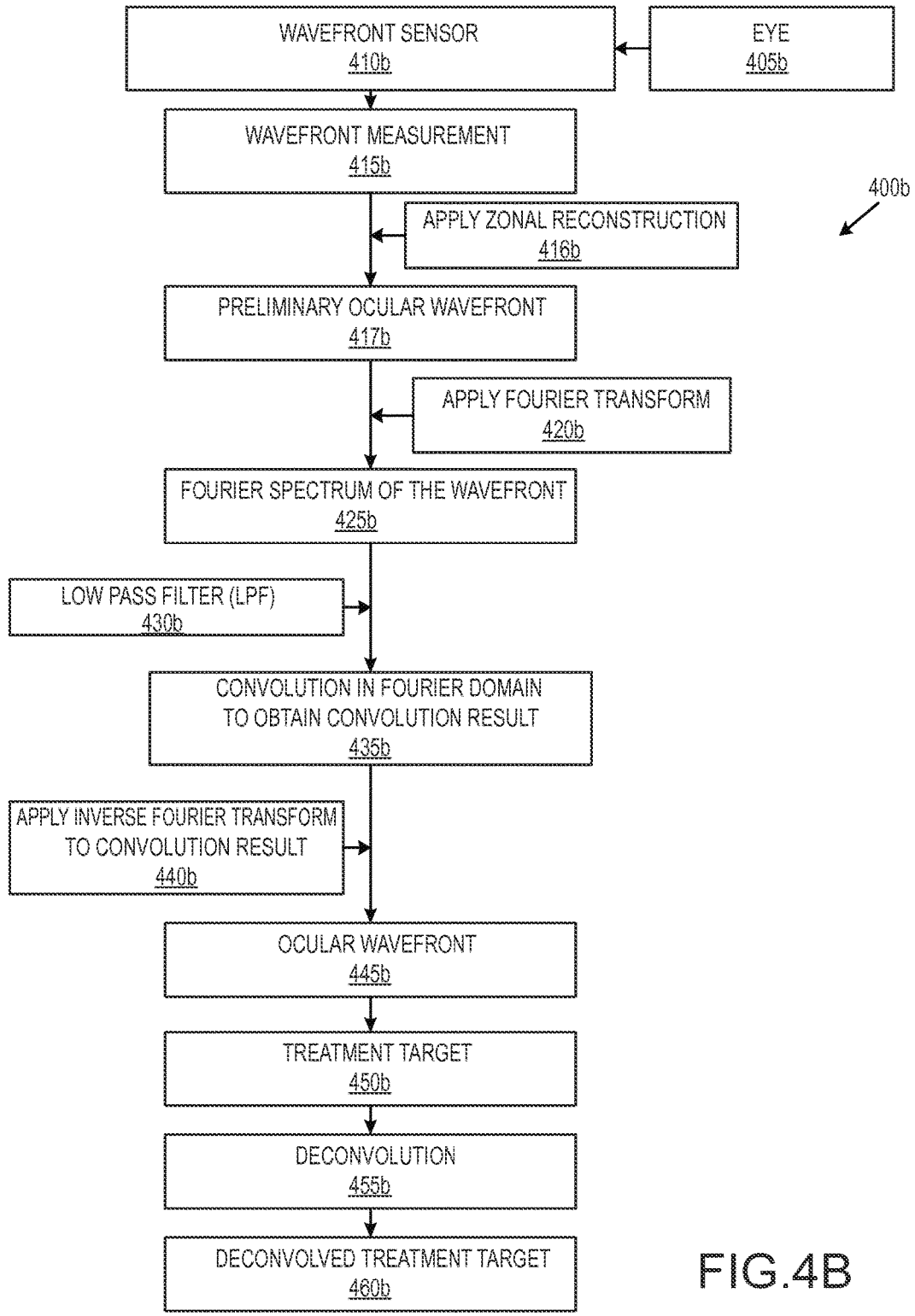
FIG. 4B depicts aspects of wavefront measurement processing according to embodiments of the present invention.

According to some embodiments, a zonal reconstruction technique can be used as an alternative to a Fourier reconstruction technique. Hence, as depicted in FIG. 4B, an exemplary method 400b of generating at treatment target or plan can include obtaining a wavefront measurement 415b for an eye 405b of a patient. Often, the eye may present high spatial frequency features, including transient features such as tear film, as well as permanent features such as corneal scars. As discussed elsewhere herein, it is possible to ignore or filter out certain small-scale spatial variations. The wavefront measurement 415b may be obtained, for example, by evaluating the eye 405b with a wavefront sensor device 410b. A wavefront sensor 410b may include an array of lenslets, and the configuration of the lenslet array can determine the resolution of the sensor. For example, a lower density resolution sensor may have a lenslet array with wider spacing, and a higher density resolution sensor may have a lenslet array with narrower spacing. The wavefront sensor 410b can be configured to detect high spatial frequency features, including rapid curvature changes and the like. As discussed elsewhere herein, embodiments of the present invention can operate to ignore or suppress certain high spatial frequency information obtained by the wavefront device. In some instances, a filter can be used to suppress this information, in a way that is consistent for all measurements (e.g. independent of the resolution of the sensor, and independent of the wavefront diameter). Hence, a wavefront measurement having a very high resolution can be processed with a Fourier transform (or some other zonal reconstruction methods), and an LPF filter can be applied according to a defined spatial scale for smoothing. According to some embodiments, the wavefront measurement can include gradient information. For example, slope sensors of the wavefront sensor 410b can operate to generate local gradient measurements. Relatedly, the wavefront measurement can include a wavefront gradient field based on the local gradients.

Techniques for wavefront construction using wavefront slope measurements can include modal reconstruction approaches (e.g. Fourier and Zernike) such as those depicted in FIG. 4, and zonal reconstruction approaches such as those depicted in FIG. 4B. Modal approaches can involve expanding the wavefront into a set of orthogonal basis functions and determining the coefficients of the set of basis functions based on the discrete phase-slope measurements. Zonal approaches can involve determining the wavefront directly based on the set of discrete phase-slope measurements. Exemplary modal and/or zonal reconstruction techniques are discussed in U.S. Pat. No. 7,335,867 and U.S. Patent Publication Nos. 2005/0012898, 2007/0058132, 2007/0091263, 2007/0222948, 2008/0140329, 2011/0149239, and 2011/0301582, and the use of modal reconstruction with Zernike polynomials, as well as a comparison of modal and zonal reconstructions, has been discussed in detail by W. H. Southwell, "Wave-front estimation from wave-front slope measurements," J. Opt. Soc. Am. 70:998-1006 (1980). The content of each of the above references is incorporated herein by reference.

As shown in FIG. 4B, embodiments of the present invention can involve processing a wavefront measurement 415b (e.g. a slope or gradient field obtained from an aberrometer), by applying a zonal reconstruction 416b to obtain a preliminary ocular wavefront 417b. In this way, the preliminary ocular wavefront 417b, which can be in the spatial domain, is based on direct use of slope or gradient information for each lenslet of the aberrometer array. Aberrometers having fine lenslet spacing are well suited for use in detecting small features, thus resulting in the presence of high spatial frequency features in the ocular wavefront.

The preliminary ocular wavefront 417b obtained via zonal reconstruction may include high spatial frequency features as a result of the reconstruction. For example, the zonal reconstruction method may produce non-smooth connections between zones, or there may be large changes in curvature between zones or at the interface between two adjacent zones. Hence, an abrupt change (e.g. in height or tilt) in the reconstructed wavefront between neighboring zones can represent high spatial frequency information. As discussed elsewhere herein, such high spatial frequency features can be smoothed out with a low-pass filter. In some embodiments, another interpolation technique (e.g. other than zonal reconstruction) can be used to determine the preliminary ocular wavefront 417b, and high spatial frequency features or artifacts present in the preliminary ocular wavefront 417b can be smoothed out with a low pass filter.

As depicted as step 420b, methods may include applying a Fourier transform to the preliminary ocular wavefront 417b, so as to obtain a Fourier transform 425b of the wavefront. In this way, spatial domain representation of wavefront 417b can be converted to the Fourier domain. For example, by applying the Fourier transform of step 420b, it is possible to obtain a Fourier transform of the zonally reconstructed wavefront. A Fourier transform can be used to reconstruct wavefront data by decomposing the image into spatial frequency components. As noted elsewhere herein, the Fourier spectrum of the wavefront 425b can provide a high resolution representation of the wavefront.

According to step 430b, methods may also include provising a low pass filter (LPF), which can operate to remove high spatial frequency data or variations of the wavefront. In some cases, a Gaussian kernel may be used. In some cases, a single parameter Butterworth kernel may be used. In some cases, a dual parameter or multiple parameter kernel may be used. Exemplary filter, kernels, and related techniques are discussed in U.S. Patent Application No. 61/708,815 filed Oct. 2, 2012, U.S. Patent Application No. 61/871,120 filed Aug. 28, 2013, U.S. patent application Ser. No. 14/044,650 filed Oct. 2, 2013, and U.S. Patent Application No. 61/901,216 filed Nov. 7, 2013, the contents of each of which are incorporated herein by reference.

The low pass filter (LPF) can be used to remove or reduce small-scale spatial variations (e.g. high spatial frequency features) associated with the measured wavefront, for example by processing the measured wavefront information with LPF prior to using the measured wavefront information in the treatment planning protocol. Typically, although the small-scale spatial variations are removed, the low order and high order aberration information is retained. According to some embodiments, a Gaussian low-pass filter having a kernel size of 0.3 mm can be used. Such a filter produced little or no change in the low-order and high-order aberrations, and can smooth out any features smaller than 0.3 mm, thus improving the robustness and efficiency of the generated treatment.

In some cases, the smoothing kernel size may correspond to a spatial frequency cutoff in the frequency domain. For example, with a pupil that is 6 mm in diameter (which is typical), the Airy disk can be about 0.38 arc minutes, which corresponds to about 79 cycles per degree (cutoff frequency) in the frequency domain. If the aberrometer lenslet spacing is 0.175 mm or so, a 0.3 mm in size on the cornea corresponds to about 0.3/0.175, or 1.7 times the lenslet spacing. Therefore, 0.3 mm can correspond to 1.7 times smaller than the cutoff frequency of 79 cpd, which is about 46 cpd. Hence, using a low pass filter kernel size of 0.3 mm for a 6 mm pupil (or measured wavefront diameter) can suppress or remove high spatial frequency structures that are higher than about 46 cpd.

According to some embodiments, this cutoff number can change with different pupil sizes. For example, with a smaller pupil, this 0.3 mm (i.e. kernel size) is a bigger relative portion so it corresponds to a lower frequency number. For example, for a 5 mm pupil, 0.3 mm corresponds to only about 38 cpd. Hence, using a low pass filter kernel size of 0.3 mm for a 5 mm pupil (or measured wavefront diameter) can suppress or remove high spatial frequency structures that are higher than about 38 cpd.

For a very small pupil, say, 2 mm in diameter, 0.3 mm corresponds to 15 cpd, which is not very high spatial frequency. 15 cpd corresponds to about 20/40 in visual acuity. According to some embodiments, for a pupil size of 4 mm or smaller, it may be desirable to use a smoothing kernel size that is different from 0.3 mm, since the smoothing in principle may inhibit the correction better than 30 cpd, or 20/20. Typically, however, patients rarely present with a pupil size (or a measured wavefront diameter) smaller than 4 mm.

Use of a 0.3 mm cutoff scale can be based on physiological parameters. For example, scales of this size or smaller can eventually disappear during after-treatment healing. Hence, it may not be desirable to ablate the cornea with a target that has features smaller than 0.3 mm. In some cases, a low pass filter can be applied to remove high spatial frequency structures within a certain range of sizes or dimensions, between an upper threshold and a lower threshold. For example, it is possible to apply a band-pass filter to limit certain sections of frequencies. In some cases, a lower threshold can have a value that is greater than the 0 frequency. In some cases, a low pass filter can operate to limit a spatial frequency band, for example to dampen artificial noises introduced by a wavefront device.

In some instances, the low pass filter can be based on various factors, including the ability of the laser to ablate, the actual smoothing of the cornea after surgery, tracking and/or registration features of the laser delivery system, and the like. For example, it is possible to define the spatial dimension of the filter in a way that takes into account the cell sizes, the epithelial layer, or other biological parameters.

Embodiments of the present invention encompass systems and methods for implementing the low pass filter in the Fourier domain. For example, when a wavefront is reconstructed from a Fourier spectrum, small-scale spatial features of the measured wavefront can be reduced or removed when the wavefront spectrum is multiplied by the LPF spectrum.

As shown in step 435b, methods can include performing a convolution in the Fourier domain (e.g. spectral domain or frequency domain). For example, methods may include multiplying the wavefront spectrum provided in step 425 and the LPF spectrum provided in step 430b, so as to obtain a convolution result. According to some embodiments, a corresponding convolution may also be performed in the spatial domain, rather than in the Fourier domain. For example, a convolution operation in the spatial domain can involve a multiplication step. In contrast, a convolution in the Fourier domain can involve a Fourier transform of the objects to be convolved, followed by a multiplication step that involves multiplying the Fourier spectrum components (e.g. convolution kernel or low pass filter multiplied by Fourier transform of wavefront) on a pixel by pixel basis, followed by an inverse Fourier transform step. The inverse Fourier transform can operate to transform the frequency domain function to a spatial domain function. The pre-smoothing technique can operate to attenuate or suppress the high spatial frequency features.

As shown in step 440*b*, methods can further include applying an inverse Fourier transform to the convolution result obtained in step 435*b*. In this way, it is possible to obtain the ocular wavefront 445*b*. Hence, the ocular wavefront can represent a reconstructed gradient field, which is provided by obtaining the inverse Fourier transform of the Fourier transform. According to some embodiments, the Fourier transform can be represented by the convolution result 435*b*. Put another way, by applying the inverse Fourier transform, it is possible to obtain the ocular wavefront 445*b*, which can be considered to be a low pass filtered version (spatial domain) of the preliminary ocular wavefront 417*b* (spatial domain).

Further, methods can include determining a treatment target 450*b* based on the ocular wavefront, and applying a deconvolution to the treatment target as indicated by step 455*b*, so as to obtain a deconvolved treatment target 460*b*. Exemplary deconvolution techniques are discussed in U.S. Patent Application No. 61/708,815 filed Oct. 2, 2012, U.S. Patent Application No. 61/871,120 filed Aug. 28, 2013, U.S. patent application Ser. No. 14/044,650 filed Oct. 2, 2013, and U.S. Patent Application No. 61/901,216 filed Nov. 7, 2013, the contents of each of which are incorporated herein by reference. In some instances, the deconvolution technique can be selected based on a model of what occurs in the eye following surgery. For example, the deconvolution procedure of step 455*b* can operate to account for healing and biomechanical changes. In some instances, a deconvolution process 455*b* can operate to amplify small-scale spatial features. Hence, a pre-smoothing protocol to obtain the ocular wavefront 445*b* can be helpful to avoid the presence of such small-scale spatial features, which may pertain to transient high spatial frequency information, when performing the deconvolution.

According to some embodiments, a treatment target 450*b* can be used for laser surgery, without performing the deconvolution process of step 455*b*.

Figure 5:
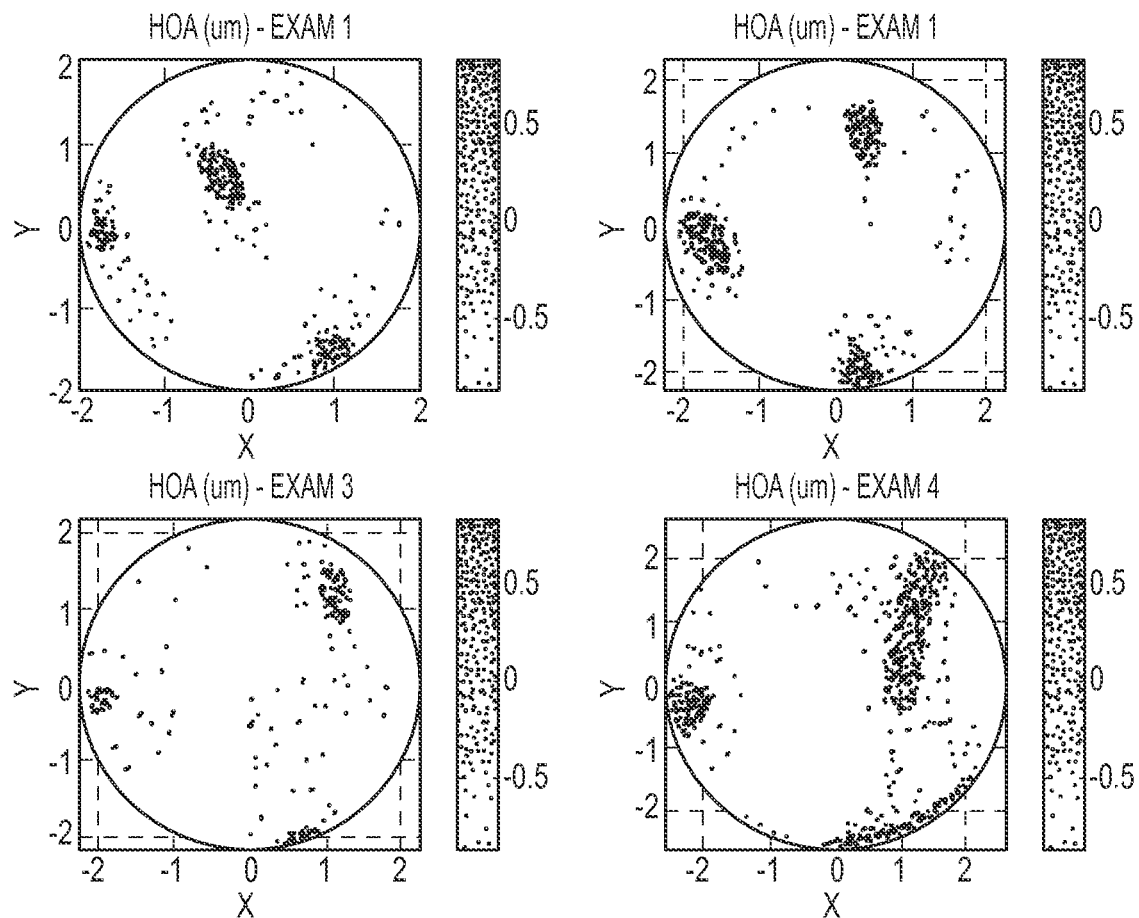
FIG. 5 illustrates high order aberrations (HOA) or errors for sequential wavefront measurements for an eye, according to embodiments of the present invention.

As noted above, embodiments of the present invention encompass systems and methods for filtering out small-scale variations of a wavefront measurement. Often, such variations are transient, and can appear and disappear from one wavefront measurement to another, particularly when taking multiple wavefront measurements from a single eye, one of which can be used for generating a treatment plan. For example, FIG. 5 depicts high order aberrations (HOA) or errors for sequential wavefront measurements for a myopic eye (Sphere=−6.75D, Cylinder=−1.5D). The wavefront errors can be shown in μm as deviations from an average over multiple sequential measurements. For treatment planning purposes, it may be desirable to not take into account such transient small-scale features. The techniques disclosed herein provide approaches for reducing, eliminating, or filtering out such transient small-scale spatial variations from the wavefront before using the wavefront in a treatment plan. In this way, the refractive surgery can be designed to address systemic errors in the wavefront rather than the randomly appearing fluctuations.

According to some embodiments, small-scale variations in the ablation profile do not affect the long-term treatment result or vision quality. Such variations can disappear on the cornea several months after surgery, for example when the epithelium covers up the small-scale variations during post-treatment cornea healing. The LASIK flap can also drape small-scale ablation features and smooth the cornea anterior surface. It is possible to generate treatment plan which does not involve such small-scale variations in the ablation profile. For example, such features can be filtered from a wavefront measurement before the treatment is generated. In other words, although the wavefront measurement may include high spatial frequency information (e.g. corresponding to small-scale variations in the measurement), such information can be disregarded or filtered when determining the laser treatment. By not including such small-scale spatial variations in the treatment plan, unnecessary ablation features and/or ablation features which are present for only a limited period of time can be avoided.

Wavefront measuring devices (e.g. aberrometers) typically have a finite spatial resolutions, for example from 0.1 to 0.2 mm. According to some embodiments, Fourier decomposition techniques can be used for wavefront reconstruction with high resolutions. Wavefront features in a restored wavefront having a scale smaller than the aberrometer resolution may represent artifacts, and such artifacts can be suppressed, disregarded, or filtered out when developing a refractive treatment plan based on the wavefront measurement.

In some instances, certain small-scaled features in a treatment target may be artifacts which are introduced by inaccuracies of a treatment planning algorithm. Such artifacts may be more prevalent in or near the transition zone. These artifact features do not represent real structures in the wavefront. Embodiments of the present invention encompass treatment target generation techniques which do not introduce such artifacts into the treatment target.

Small-scaled wavefront errors may have little or no effect on vision quality. In some instances, sharp wavefront features representing stable corneal defects (e.g. corneal scars) can be resolved if the resolution of the aberrometer is sufficiently high.

Embodiments of the present invention encompass wavefront-based treatment planning systems and methods which can suppress or totally ignore high spatial frequency information or small-scale features in the wavefront measurement. Relatedly, systems and methods as disclosed herein can be used to generate ablation treatment plans which correct only wavefront errors with limited scales.

According to some embodiments, transient wavefront features can be removed from a treatment plan averaging multiple wavefront measurements. Because the transient features appear and disappear from one measurement to another, they can make little contribution to the average wavefront. For example, randomly appearing an disappearing features as shown in the multiple wavefront measurements of FIG. 5 can be considered as random noise, and systems and methods which operate to average multiple wavefront measurements can reduce the effect of such random noise.

According to some embodiments, small-scale transient wavefront features can be dampened by using a weighted average of multiple wavefront measurements. The weights can be selected inversely proportional to the measurement variances. For such techniques, an objective estimate of a variance can be provided either for each pixel or for each amplitude of measurement decomposition into a set of orthogonal functions. According to some embodiments, systems and methods that implement a weighted average of multiple wavefront measurements can involve estimating the weight for each pixel measurement separately. Exemplary weighted averaging techniques which can be implemented in embodiments of the present invention are discussed in U.S. patent application Ser. No. 13/796,513 filed Mar. 12, 2013, the content of which is incorporated herein by reference.

Figure 6A:
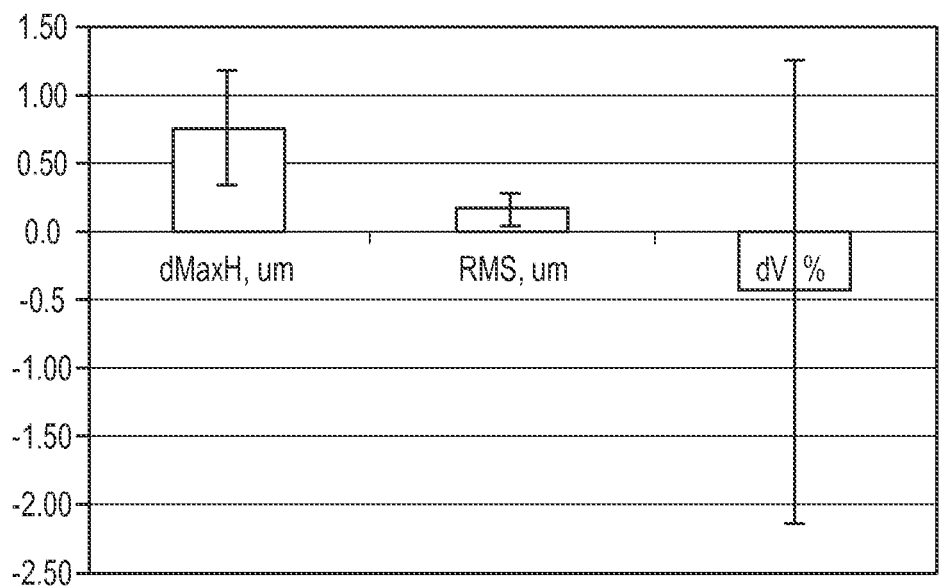
FIGS. 6A and 6B show effects of wavefront smoothing using a low pass filter, according to embodiments of the present invention.
Figure 6B:
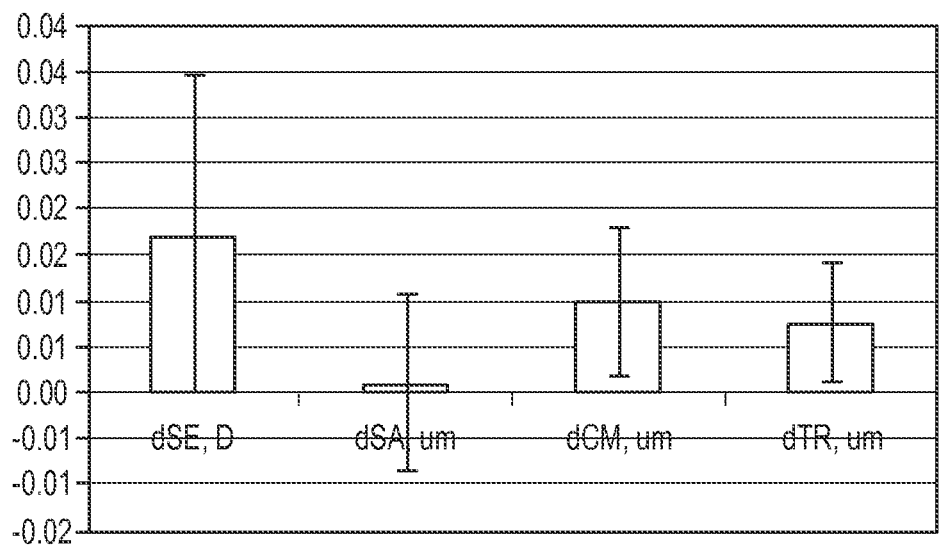

As discussed elsewhere herein, certain low pass filters can produce little or no change in the low-order and high-order aberrations, and yet can reduce or eliminate high frequency spatial features of the measured wavefront. For example, FIGS. 6A and 6B show the effect of wavefront smoothing using a low pass filter having a 0.3 mm kernel scale on ablation targets (n=98). Mean values and standard deviations are shown for changes of maximum depth (dHmax, µm), root mean squate of target change (RMS, µm), and ablated tissue volume (dV %) in FIG. 6A, and for changes in 4 mm spherical equivalent (dSE, D), and 6 mm high order aberrations: spherical aberration (dSA, µm), coma (dComa or dCM, µm), and trefoil (dTrefoil or dTR, µm) in FIG. 6B. Hence, it can be seen that such filters can smooth out small-scale spatial features (e.g. smaller than 0.3 mm), while introducing little or no change in low-order and high-order aberrations, and can also decrease maximum ablation depth and the volume of ablated tissue. As depicted in the statistics of profile changes presented in FIGS. 6A and 6B, the wavefront smoothing makes little effect on the ablation profile.

According to some embodiments, the low pass filter smoothing can be applied to only high order portions of the wavefront measurement, and the result can be re-scaled to maintain the same refraction. Accordingly, only high order aberrations can be affected and changes of low order aberrations can be minimal. In mathematical terms, the entire wavefront can be decomposed into low order and high order components. If convolved with a kernel, the whole wavefront can be expressed as a combination or summation of a convolution to the low orders and a convolution to the high orders. Accordingly, certain techniques can involve convolving the high order portion, and combining the convolved high order portion with the unconvolved low order portion. Often, some aspects of low order aberrations can be altered following kernel convolution, which can potentially change the refraction. Hence, it may be desirable to pre-smooth only the high order aberration portion of the wavefront measurement, and then combine the pre-smoothed high order aberration portion with the unsmoothed low order aberration portion.

In some instances, low pass filtering techniques can be used with corneal topography data, because very short-scale features often represent measurement noises, transients (e.g. tear film changes), or image restoration artifacts. The filtering techniques can be used to reduce high spatial frequency features of the topography data.

All patent filings (including patents, patent applications, and patent publications), scientific journals, books, treatises, technical references, and other publications and materials discussed in this application are incorporated herein by reference in their entirety for all purposes.

A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present invention may be provided in one or more kits for such use. The kits may comprise a system for determining a treatment for an eye of a patient, and instructions for use. Optionally, such kits may further include any of the other system components described in relation to the present invention and any other materials or items relevant to the present invention. The instructions for use can set forth any of the methods as described herein.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of generating a vision treatment target for an eye of a patient, comprising:
   receiving, at a processor, a wavefront measurement for the eye of the patient;
   executing, on the processor, computer executable code stored on a non-transitory computer readable medium, the computer executable code comprising instructions that when executed on the processor cause the processor to process the wavefront measurement, using a low pass filter, to obtain an ocular wavefront; and generating the vision treatment target based on the ocular wavefront.

2. The method according to claim 1, wherein the instructions that cause the processor to process the wavefront measurement comprise instructions that when executed on the processor cause the processor to:

apply a Fourier transform to the wavefront measurement to obtain a Fourier spectrum of the wavefront;

convolve, in the Fourier domain, the Fourier spectrum of the wavefront and the low pass filter to obtain a Fourier spectrum convolution result; and apply an inverse transform to the convolution result to obtain the ocular wavefront, wherein the ocular wavefront represents a low pass filtered version of the wavefront measurement, such that high spatial frequency features present in the wavefront measurement are not present in the ocular wavefront.

3. The method according to claim 2, wherein the low pass filter is a Gaussian low-pass filter having a kernel size of 0.3 mm.

4. The method according to claim 1, further comprising administering the vision treatment target to the eye of the patient.

5. The method according to claim 1, further comprising processing the treatment target with a deconvolution protocol to obtain a deconvolved treatment target.

6. The method according to claim 5, further comprising administering the deconvolved treatment target to the eye of the patient.

7. A system for generating a vision treatment target for an eye of a patient, comprising:

a processor;

a first module comprising a tangible medium embodying machine-readable code executed on the processor to obtain a wavefront measurement for the eye of the patient;

a second module comprising a tangible medium embodying machine-readable code executed on the processor to process the wavefront measurement with a low pass filter to obtain an ocular wavefront; and a third module comprising a tangible medium embodying machine-readable code executed on the processor to generate the vision treatment target based on the ocular wavefront.

8. The system according to claim 7, wherein the tangible medium embodying machine-readable code of the second module, when executed on the processor, applies a Fourier transform to the wavefront measurement to obtain a Fourier spectrum of the wavefront, convolves, in the Fourier domain, the Fourier spectrum of the wavefront and the low pass filter to obtain a Fourier spectrum convolution result, and applies an inverse transform to the convolution result to obtain the ocular wavefront, and wherein the ocular wavefront represents a low pass filtered version of the wavefront measurement, such that high spatial frequency features present in the wavefront measurement are not present in the ocular wavefront.

9. The system according to claim 8, wherein the low pass filter is a Gaussian low-pass filter having a kernel size of 0.3 mm.

10. The system according to claim 7, further comprising a fourth module comprising a tangible medium embodying machine-readable code executed on the processor to administer the vision treatment target to the eye of the patient.

11. The system according to claim 7, further comprising a fourth module comprising a tangible medium embodying machine-readable code executed on the processor to process the treatment target with a deconvolution protocol to obtain a deconvolved treatment target.

12. The system according to claim 11, further comprising a fifth module comprising a tangible medium embodying machine-readable code executed on the processor to administer the deconvolved treatment target to the eye of the patient.

13. A computer product embodied on a tangible computer readable storage medium, comprising:

code for obtaining a wavefront measurement for the eye of the patient;

code for processing the wavefront measurement, using a low pass filter, to obtain an ocular wavefront; and code for generating the vision treatment target based on the ocular wavefront.

14. The computer product according to claim 13, wherein the code for processing the wavefront measurement comprises:

code for applying a Fourier transform to the wavefront measurement to obtain a Fourier spectrum of the wavefront;

code for convolving, in the Fourier domain, the Fourier spectrum of the wavefront and the low pass filter to obtain a Fourier spectrum convolution result; and code for applying an inverse transform to the convolution result to obtain the ocular wavefront, wherein the ocular wavefront represents a low pass filtered version of the wavefront measurement, such that high spatial frequency features present in the wavefront measurement are not present in the ocular wavefront.

15. The computer product according to claim 14, wherein the low pass filter is a Gaussian low-pass filter having a kernel size of 0.3 mm.

16. The computer product according to claim 13, further comprising code for administering the vision treatment target to the eye of the patient.

17. The computer product according to claim 13, further comprising code for processing the treatment target with a deconvolution protocol to obtain a deconvolved treatment target.

18. The computer product according to claim 17, further comprising code for administering the deconvolved treatment target to the eye of the patient.

* * * * *